(12) United States Patent
Pizza et al.

(10) Patent No.: US 12,109,259 B2
(45) Date of Patent: Oct. 8, 2024

(54) **VACCINES FOR *NEISSERIA GONORRHOEAE***

(71) Applicant: GLAXOSMITHKLINE BIOLOGICALS, S.A., Rixensart (BE)

(72) Inventors: Mariagrazia Pizza, Siena (IT); Steven B. Black, Berkeley (CA)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 5 days.

(21) Appl. No.: 16/326,833

(22) PCT Filed: Sep. 1, 2017

(86) PCT No.: PCT/EP2017/072009
§ 371 (c)(1),
(2) Date: Feb. 20, 2019

(87) PCT Pub. No.: WO2018/042015
PCT Pub. Date: Mar. 8, 2018

(65) Prior Publication Data
US 2019/0282684 A1 Sep. 19, 2019

Related U.S. Application Data

(60) Provisional application No. 62/383,134, filed on Sep. 2, 2016.

(51) Int. Cl.
| | | |
|---|---|---|
| *A61K 39/095* | (2006.01) | |
| *A61K 39/116* | (2006.01) | |
| *A61K 39/39* | (2006.01) | |
| *A61K 47/64* | (2017.01) | |
| *C07K 14/22* | (2006.01) | |
| *C07K 16/12* | (2006.01) | |
| *A61K 39/00* | (2006.01) | |

(52) U.S. Cl.
CPC .......... *A61K 39/095* (2013.01); *A61K 39/116* (2013.01); *A61K 39/39* (2013.01); *A61K 47/646* (2017.08); *C07K 14/22* (2013.01); *C07K 16/1217* (2013.01); *A61K 2039/54* (2013.01); *A61K 2039/55* (2013.01); *A61K 2039/55505* (2013.01); *A61K 2039/58* (2013.01); *C07K 2317/33* (2013.01)

(58) Field of Classification Search
None
See application file for complete search history.

(56) References Cited

U.S. PATENT DOCUMENTS

| | | | | |
|---|---|---|---|---|
| 4,186,182 | A * | 1/1980 | Gaafar | |
| 9,259,462 | B2 | 2/2016 | Serruto et al. | |
| 9,764,027 | B2 * | 9/2017 | Grandi | A61K 39/092 |
| 10,179,167 | B2 | 1/2019 | Serruto et al. | |
| 10,376,573 | B2 | 8/2019 | Pizza et al. | |
| 2005/0222385 | A1 * | 10/2005 | Pizza | C07K 14/22 |
| | | | | 530/350 |
| 2008/0063665 | A1 * | 3/2008 | Oster | A61K 39/095 |
| | | | | 424/232.1 |
| 2013/0022639 | A1 * | 1/2013 | Oriente | A61P 31/04 |
| | | | | 424/250.1 |
| 2013/0236489 | A1 | 9/2013 | Serruto et al. | |
| 2015/0291666 | A1 | 10/2015 | Jerse et al. | |
| 2016/0166674 | A1 | 6/2016 | Pizza et al. | |

FOREIGN PATENT DOCUMENTS

| | | |
|---|---|---|
| EP | 1977761 A2 | 10/2008 |
| JP | 2003-518363 A | 6/2003 |
| JP | 2007-508537 A | 4/2007 |
| JP | 2013-521770 A | 6/2013 |
| WO | 2000066741 A2 | 11/2000 |
| WO | 2005/035733 A2 | 4/2005 |
| WO | 2005032583 A2 | 4/2005 |
| WO | 2011110634 A1 | 9/2011 |
| WO | 2018042017 A2 | 3/2018 |

OTHER PUBLICATIONS

Cuello et al. VacciMonitor 2009 vol. 18 No. 2 pp. 76-78.*
Panatto et al The Indian Journal of Medical Research Dec. 2013; 138(6): 835-846.*
Dehne et al. Sexually Transmitted Infections Among Adolescents The Need for Adequate Health Services. World Health Organization 2005. 93 pages.*
Kidd et al. Clin. Infect. Dis. 61: Suppl. 8: S785-S801, Sep. 18, 2015.*
Mameli et al. Future Microbiol. (2015) 10(1), 1579-1598.*
Thomson Reuters One (pp. 1-3, Feb. 24, 2014).*
Santolaya et al. Lancet 2012; 379:617-24.*
Petousis-Harris et al. Lancet. Jul. 10, 2017; 390:1603-1610.*
Meningococcal B Immunisation Evaluation Final Report CBG Health Research Nov. 2006 retrieved Nov. 7, 2022 from https://www.health.govt.nz/system/files/documents/publications/menzb-implementation-evaluation-nov06.pdf.*
Oster et al. Vaccine 23 (2005) 2191-2196.*
Valenzuela et al. Vaccine Jul. 14, 2005;23(32):4110-9.*
Acevedo et al: "Bacterial Outer Membrane Vesicles and Vaccine Applications", Frontiers in Immunology, vol. 5; No. 121; 2014; pp. 1-6.
Chen, et al., "Adherence of pilus-Opa+gonococci to epithelial cells in vitro involves heparin sulfate", 1995 The Journal of Experimental Medicine 182(2):511-517.
Cremieux et al., "Bactericidal Antibodies Against Neisseria Gonorrhoeae Elicited by Neisseria Meningitidis", The Lancet, vol. 324, No. 8408, 1984, p. 930.
Gokhale, "Struggling Vaccines From Novartis Turn Into Sales Boon for Glaxo", Aug. 31, 2016 article in Bloomberg Business; available at https://www.bloomberg.com/news/articles/2016-08-31/struggling-vaccines-from-novartis-turn-into-sales-boon-for-glaxo; last visited May 21, 2019; 3 pages.
Li et al., "Neisseria gonorrhoeae NspA Induces Specific Bactericidal and Opsonic Antibodies in Mice", Clinical and Vaccine Immunology, vol. 18, No. 11, 2011, pp. 1817-1822.

(Continued)

*Primary Examiner* — Oluwatosin A Ogunbiyi

(57) ABSTRACT

A method for immunizing a subject in need thereof against *Neisseria gonorrhoeae* by administering an immunogenic composition comprising meningococcal outer membrane vesicles (OMVs).

16 Claims, 9 Drawing Sheets

(56) References Cited

OTHER PUBLICATIONS

Liu et al., "Experimental vaccine induces Th1-driven immune responses and resistence to Neisseria gonorrhoeae Infection in a murine model", Mucosal Immunology, vol. 10, No. 6; 2017; pp. 1594-1608.
Muzzi et al., "Conservation of Meningococcal Antigens in the Genus Neisseria", mBIO, vol. 4, No. 3, 2013, pp. e00163-13.
Perera et al: "The role of pili and outer membrane vesicles in the immunogenicity of Neisseria gonorrhoeae in the guinea pig chamber model", FEMS Microbiology Letters, Wiley-Blackwell Publishing Ltd, GB, vol. 17, No. 1-3, 1983, pp. 303-306.
Perez et al., "Heterologous Prime-Boost Immunization with VA-Mengoc-BC and AFCo1 Elicits Systemic and Mucosal Immunity to Neisseria meningitides and N gonorrhoeae", Revista VacciMonitor, 2010, pp. 1-2.
Perez et al., "Mucosal approaches in Neisseria Vaccinology", VacciMonitor; vol. 18, No. 2; 2009, pp. 53-55.
Perez, et al., "Natural Neissera Derive Proteoliposome and Cochleate as Potent Vaccine Adjuvants", Pharmacologyonline, 2006, pp. 762-764.
Petousis-Harris et al: "Abstract: Effectiveness of a Group B Omv Meningococcal Vaccine on Gonorrhoea in New Zealand—a Case Control Study (2016 National STD Prevention Conference)", 2016 (Sep. 21, 2016), p. 1.
Plante et al., "Intranasal Immunization with Gonococcal Outer Membrane Preparations Reduces the Duration of Vaginal Colonization of Mice by Neisseria gonorrhoeae", The Journal of Infectious Diseases, 2000, pp. 848-855.
Price et al., "Intranasal Administration of Recombinant Neisseria gonorrhoeae Transferrin Binding Proteins A and B Conjugated to the Cholera Toxin B Subunit Induces Systemic and Vaginal Antibodies in Mice", Infection and Immunity, vol. 73, No. 7, 2005, pp. 3945-3953.
Regnier, et al., "Potential impact of vaccination against Neisseria meningitidis on Neisseria gonorrhoeae in the United States: Results from a decision-analysis model", Human Vaccines and Immunotherapeutics, vol. 10, No. 12, 2014 (Nov. 1, 2014), pp. 3737-3745.
Rippa et al., "Molecular Engineering of Ghfp, the Gonococcal Orthologue of Neisseria meningitides Factor H Binding Protein", Clinical and Vaccine Immunology, vol. 22, No. 7, 2015, pp. 769-777.
Seib et al., "Characterization of Diverse Subvariants of the Meningococcal Factor H (fH) Binding Protein for their Ability to Bind fH, to Mediate Serum Resistance, and to Induce Bactericidal Antibodies", Infection and Immunity, vol. 79, No. 2, 2011, pp. 970-981.
Semchenko et al., "Neisseria heparin binding antigen (NHBA): A potential vaccine candidate for Meisseria gonorrhoeae", 2015; p. 1.
Whelan et al: "Ecologic Study of Meningococcal B Vaccine and Neisseria gonorrhoeae Infection, Norway", Emerging Infectious Diseases, vol. 22, No. 6, 2011 (Nov. 16, 2011), pp. 1137-1139.
Zhu et al., "Comparison of Immune Responses to Gonococcal PorB Delivered as Outer Membrane Vesicles, Recombinant Protein, or Venezuelan Equine Encephalitis Virus Replicon Particles", Infection and Immunity, vol. 73, No. 11, 2005, pp. 7558-7568.
Cuello et al., "Nasal Immunization with AFCo1 Induces Immune Response to N. gonorrhoea in Mice", VacciMonitor, vol. 18, No. 2, 2009, pp. 76-78.
Panatto et al., "New Versus Old Meningococcal Group B Vaccines: How the new ones may benefit infants and toddlers", Indian Journal of Mesdical Reserach, vol. 138. No. 6, 2013, pp. 835-846.
Gokhale, Business "Struggling Vaccine for Novartis turn into Sales Boon for Glaxo" Aug. 30, 2016.
Semchenko et al., Clinical Infectious Diseases, 69(7): 1101-1111 (2019).
Whelan et al., Emerging Infectious Diseases, 22(6): 1137-1139 (2016).
GBD 2015 Disease and Injury Incidence and Prevalence Collaborators, "Global, regional, and national incidence, prevalence, and years lived with disability for 310 diseases and injuries, 1990-2015: a systematic analysis for the Global Burden of Disease Study 2015." Lancet (2016) 388:1545-602.
Read et al. Lancet (2014) 384: 2123-2131.
Morbidity and Mortality Weekly Report (MMWR), CDC (2015), 64 (22): 608-612 (7 pages).
Toneatto et al., Hum. Vaccine (2011) 7: 646-653.
Santolaya et al., Hum. Vaccin. Immunother. (2013) 9:11 p. 2304-2310.
Todar, Kenneth, "Pathogenic Neisseriae: Gonorrhoea, Neonatal Opthalmia and Meningococcal Meningitis" in Todar's Online Textbook of Bacteriology 2008, 13 pages, available at http://textbookofbacteriology.net/neisseria_1.html.
Pogany et al., Can. Fam. Physician (2015) 61: 869-873.
Moore EW, J. Amer. Colleg Hlth (2013) 61:4, p. 196-202.
O'Ryan et al., Drugs (2014) 74:15-30.
McGuiness et al., Lancet (1991) 337: 514-517.
Skolnick et al., Trends in Biotechnology (2000) 18: 34-39.
McGuiness et al., Mol. Microbiol. (1993) 7: 505-514.
BacPath 13: Molecular Analysis of Bacterial Pathogens Conference, Poster Presentation (2015) 1 page.
Hadad et al., Novel Meningoccal 4CMenB vaccine antigens—prevalence and polymorphisms of the encoding genes in Neisseria gonorrhoeae, APMIS (2012) 120: 750-760.
Knighting et al., Health Serv. Deliv. Res. 9: 1-268, 2021.
Valenzuela, et al., Vaccine 2005, 23(32), pp. 4110-4119.
Petousis-Harris, et al., Lancet, 2017, 390; 1603-1610.
Knighting et al., Health Serv. Deliv. Res (2021) 9.6 (7 pages).

\* cited by examiner

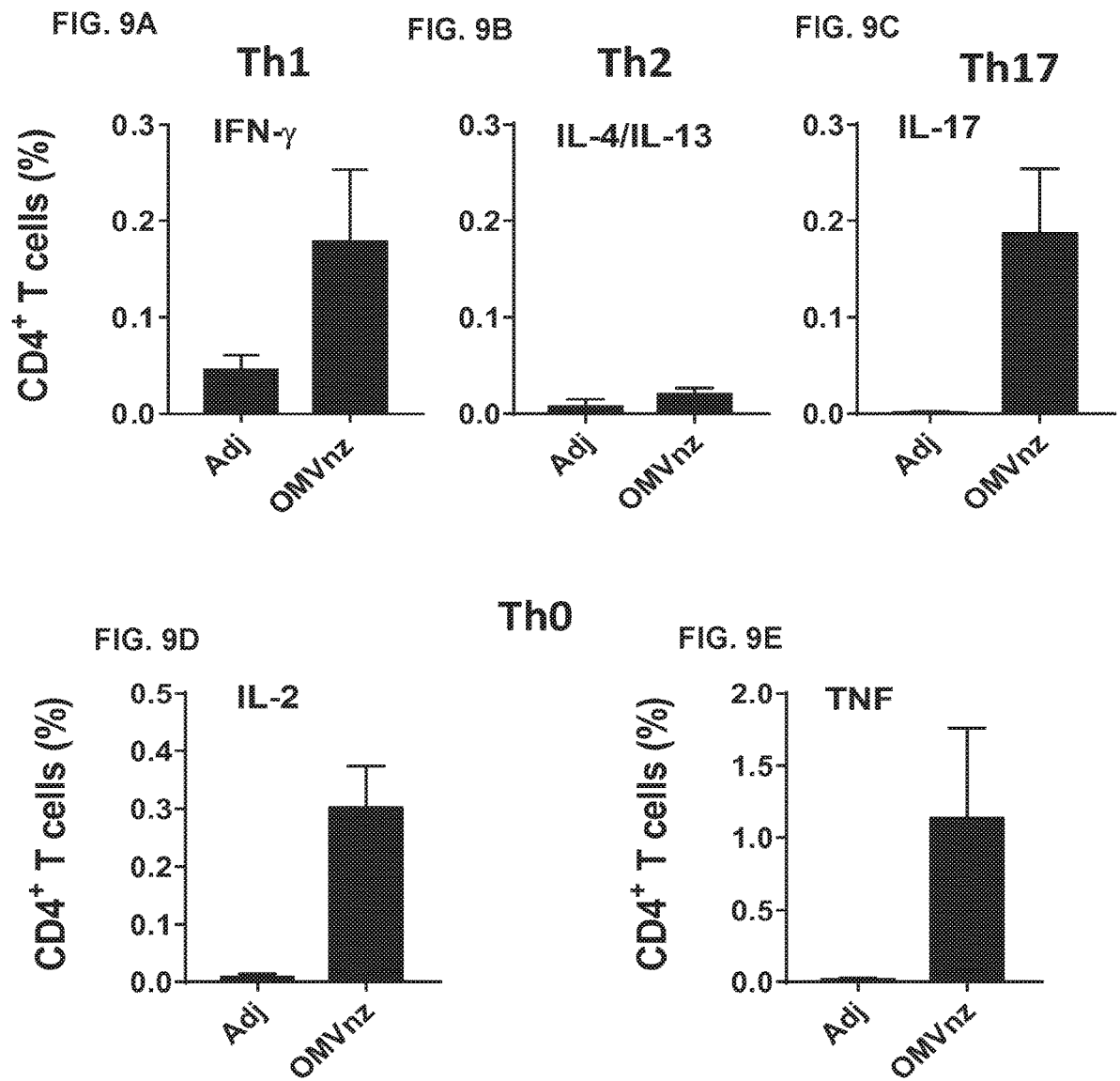

VACCINES FOR *NEISSERIA GONORRHOEAE*

TECHNICAL FIELD

This invention is in the field of vaccines for immunizing against *Neisseria gonorrhoeae*.

BACKGROUND ART

*Neisseria gonorrhoeae* and *Neisseria meningitidis* are Gram-negative bacterial pathogens. *N. gonorrhoeae* is the causative agent of gonorrhoea, whereas *N. meningitidis* causes meningitis and septicaemia.

Gonorrhoea is a major global public health concern exacerbated by multiple drug-resistance, with an estimated 78 million incident new cases each year [1]. Antimicrobial resistance of gonococci has grown steadily since the 1940s with the emergence of extensively drug-resistant strains [2,3]. Natural infection with gonorrhoea does not induce protective immunity, with repeated infection common [4]. The increase of antibiotic-resistant and untreatable gonococcal strains emphasizes the need to develop an effective vaccine.

Efforts to develop an effective vaccine against gonorrhoea have been unsuccessful despite over a century of research [5]. Challenges include the absence of a correlate of protection, lack of a suitable laboratory animal model, subversion of the immune response by the gonococcus to favour survival, and high antigenic variability. The four vaccine candidates to reach clinical trials have been whole cell (two vaccine candidates), pilin and Protein 1 vaccines, but none was effective [5,6,7]. Thus there remains a need for a vaccine which would be effective against *N. gonorrhoeae*.

Reasons for the lack of progress on vaccines for gonorrhoea include a lack of a correlate of protection, lack of a suitable laboratory model and a highly antigenically variable surface. The only trials have been the aforementioned whole cell and pilin vaccines. As recovery from infection does not confer immunity against reinfection there are unlikely to be answers from the process of natural course of infection.

While *N. gonorrhoeae* interacts with innate immune cells such as macrophage and dendritic cells and elicits inflammatory response, it suppresses the Th1/Th2 mediated specific immune responses, although a localized non-specific antibody response with no memory generated occurs [8].

One further challenge in eliciting protective immunity against *N. gonorrhoeae* is the fact that gonococcal disease is generally confined to the mucosal surface.

No link between vaccination with a meningococcal vaccine and protection against gonorrhoea has been confirmed to date, and the antigens found in meningococcal vaccines have generally been considered unsuitable for immunisation against *N. gonorrhoeae* [8].

SUMMARY OF THE INVENTION

A first aspect of the invention provides a method for immunizing a subject in need thereof against *Neisseria gonorrhoeae* by administering an immunogenic composition comprising meningococcal outer membrane vesicles (OMVs).

A second aspect of the invention provides an immunogenic composition for use in immunizing a subject in need thereof against *Neisseria gonorrhoeae*, wherein the immunogenic composition comprises meningococcal outer membrane vesicles (OMVs).

A third aspect of the invention is directed to the use of meningococcal outer membrane vesicles (OMVs) in the manufacture of a medicament for immunizing a subject in need thereof against *Neisseria gonorrhoeae*.

DISCLOSURE OF THE INVENTION

The inventors have found that subjects immunized with meningococcal outer membrane vesicle (OMV) vaccines are also protected against gonorrhoea.

OMV vaccines are generally considered useful only against epidemics dominated by strains belonging to the same meningococcal group B clonal complex. However, the inventors initially observed that among the population eligible for vaccination with the McNZB™ used in New Zealand (NZ) in 2004-2008, there was a subsequent reduction in cases of gonorrhoea among young adults aged 15-30 years (Example 1). A protective effect of the McNZB™ vaccine was subsequently found in a retrospective case control study (Example 2).

Despite the marked differences in disease manifestation, based on DNA-DNA hybridisation there is 80-90% genetic homology in primary sequences between *Neisseria gonorrhoeae* and *Neisseria meningitidis*. Most virulence factors present in one have an equivalent in the other [9], providing a biologically plausible mechanism for cross-protection. However, genetic typing alone is insufficient to predict strain coverage, even between strains of *N. meningitidis* [10].

The NZ McNZB™ vaccine was a preparation of the OMV of the epidemic strain of group B Meningococcal NZ98/254, B:4:P1.7b,4.

The inventors have now shown that meningococcal OMV from group B strain NZ98/254 (referred to herein as OMVnz) induce bactericidal antibodies against *N. gonorrhoeae* (Example 3). They have also shown that immunization with said OMVs reduces adhesion of *N. gonorrhoeae* to human cervical cells (Example 4) and induces cellular immune responses with Th1 profiles associated with faster gonococcus clearance and resistance to gonococcal infection in an animal model (Example 5).

Thus, one aspect of the invention provides a method for immunizing a subject in need thereof against *Neisseria gonorrhoeae* by administering an immunogenic composition comprising meningococcal outer membrane vesicles (OMVs).

Similarly, the invention provides an immunogenic composition for use in immunizing a subject in need thereof against *Neisseria gonorrhoeae*, wherein the immunogenic composition comprises meningococcal outer membrane vesicles (OMVs).

Also, the invention provides the use of meningococcal outer membrane vesicles (OMVs) in the manufacture of a medicament for immunizing a subject against *Neisseria gonorrhoeae*.

In preferred embodiments, the meningococcal OMVs are from serogroup B strain NZ98/254.

Protection Against *N. gonorrhoeae*

The invention is used to immunize subjects against infection and/or disease caused by *Neisseria gonorrhoeae* (e.g. gonorrhoea and related complications such as pelvic inflammatory disease, as well as asymptomatic infection with *N. gonorrhoeae*), such that recipients of the immunogenic composition mount an immune response which provides protection against infection by and/or disease due to *Neisseria gonorrhoeae* bacteria.

Therefore, immunogenic compositions according to the invention are used in prophylactic methods for immunizing subjects against infection and/or disease caused by *Neisseria gonorrhoeae*. The immunogenic compositions may also be used in therapeutic methods (i.e. to treat *Neisseria gonorrhoeae* infection).

Protection against *N. gonorrhoeae* can be measured epidemiologically e.g. in a clinical trial, but it is convenient to use an indirect measure to confirm that an immunogenic composition elicits a serum bactericidal antibody (SBA) response in recipients. In the SBA assay, sera from recipients of the composition are incubated with target bacteria (in the present invention, *N. gonorrhoeae*) in the presence of complement (preferably human complement, although baby rabbit complement is often used instead) and killing of the bacteria is assessed at various dilutions of the sera to determine SBA activity. Results observed in the SBA assay can be reinforced by carrying out a competitive SBA assay to provide further indirect evidence of the immunogenic activity of antigen(s) of interest. In the competitive SBA assay, sera from recipients of the immunogenic composition containing the antigen(s) are pre-incubated with said antigen(s), and subsequently incubated with target bacteria in the presence of human complement. Killing of the bacteria is then assessed, and will be reduced or abolished if bactericidal antibodies in the recipients' sera bind to the antigens of interested during the pre-incubation phase and are therefore not available to bind to surface antigen on the bacteria.

It is not necessary that the composition should protect against each and every strain of *N. gonorrhoeae*, or that each and every recipient of the composition must be protected. Such universal protection is not the normal standard in this field. Rather, protection is normally assessed against a panel of clinically-relevant isolates e.g. FA1090, MS11 and F62, often selected on a country-by-country basis and perhaps varying with time, and is measured across a population of recipients. Set against the backdrop that there is no vaccine currently available to protect against gonorrhoea, even a low level of cross-protection could make vaccination worthwhile. Indeed, modelling of the theoretical impact of a meningococcal vaccine on rates of *N. gonorrhoeae* infection suggest that such vaccination would be cost-effective even at a vaccine efficacy against *N. gonorrhoeae* as low as 20% (or even 10% if antibiotic resistance were to rise substantially) [11].

The Immunogenic Composition

The invention uses an immunogenic composition (e.g. a vaccine) to protect subjects against *N. gonorrhoeae*. The composition includes an immunogenic amount of meningococcal OMVs.

The composition does not include an immunogenic amount of *N. gonorrhoeae* capsular saccharide i.e. protection against *N. gonorrhoeae* cannot be explained by an anti-saccharide response. *N. gonorrhoeae* capsular saccharide is absent as free saccharide, conjugated saccharide, or membrane-located saccharide (e.g. in OMVs). Preferably, the composition is also free of unconjugated capsular saccharide from *N. meningitidis* serogroup A and/or C. The composition is non-pathogenic and does not comprise whole cells of *N. meningitidis* or *N. gonorrhoeae*.

Outer Membrane Vesicles

The meningococcal OMV component of the compositions of the invention can be any proteoliposomic vesicle obtained by disruption of or blebbing from a meningococcal outer membrane to form vesicles therefrom that retain antigens from the outer membrane. Thus this term includes, for instance, OMVs (sometimes referred to as 'blebs'), microvesicles (MVs), 'native OMVs' ('NOMVs') extracted from cells using detergent-free methods, and detergent-extracted OMVs (dOMVs), such as OMVs extracted from cells using deoxycholate treatment. Various such vesicles are known in the art (e.g. see references 12 to 26) and any of these can be included within a composition of the invention.

The mass of OMVs is measured as the amount of total protein.

Preferred meningococcal OMVs comprise a PorA serotype 1.4. Preferably, the OMVs comprise a PorA variable region epitope 1.7-2 (VR1) and/or 1.4 (VR2). OMVs comprising both of these epitopes are more preferred (i.e. P1.7-2,4). OMVs obtained from strain NZ98/254 are particularly preferred.

Further Meningococcal Antigens

A composition can include one or more further meningococcal protein antigens, such as HmbR, NspA, NhhA, App, Omp85, TbpA, TbpB, and/or Cu,Zn-superoxide dismutase.

Non-Meningococcal Antigens

A composition can include one or more non-meningococcal antigens (where the non-meningococcal antigens are not *N. gonorrhoeae* capsular saccharides as discussed above). For instance, the composition can include one or more of: (a) an antigen from *Streptococcus pneumoniae*, such as a saccharide (typically conjugated), as in the PREVNAR and SYNFLORIX products; (b) an antigen from hepatitis B virus, such as the surface antigen HBsAg; (c) an antigen from *Bordetella pertussis*, such as pertussis holotoxin (PT) and filamentous haemagglutinin (FHA) from *B. pertussis*, optionally also in combination with pertactin and/or agglutinogens 2 and 3; (d) a diphtheria antigen, such as a diphtheria toxoid; (e) a tetanus antigen, such as a tetanus toxoid; (f) a saccharide antigen from *Haemophilus influenzae* B (Hib), typically conjugated; and/or (g) inactivated poliovirus antigens.

Non-Antigen Components

In addition to the OMV antigens, an immunogenic composition of the invention typically includes a pharmaceutically acceptable carrier, and a thorough discussion of such carriers is available in reference 27.

The pH of a composition is usually between 6 and 8, and more preferably between 6.5 and 7.5 (e.g. about 7). Stable pH may be maintained by the use of a buffer e.g. a Tris buffer, a citrate buffer, phosphate buffer, or a histidine buffer. Thus a composition will generally include a buffer. A particularly preferred buffer is a histidine buffer with a pH between 6.4 and 6.7.

A composition may be sterile and/or pyrogen-free. Compositions may be isotonic with respect to humans.

A composition comprises an immunologically effective amount of OMV antigens. Further, a single dose of the composition comprises an immunologically effective amount of OMV antigens. An 'immunologically effective amount' is an amount which, when administered to a subject, is effective for eliciting an antibody response against the antigen. This amount can vary depending upon the health and physical condition of the individual to be treated, their age, the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The antigen content of compositions of the invention will generally be expressed in terms of the mass of protein per dose. A dose of 10-500 µg (e.g. 50 µg) per antigen can be useful.

Immunogenic compositions may include an immunological adjuvant. Thus, for example, they may include an aluminium salt adjuvant or an oil-in-water emulsion (e.g. a squalene-in-water emulsion). Suitable aluminium salts include hydroxides (e.g. oxyhydroxides), phosphates (e.g. hydroxyphosphates, orthophosphates), (e.g. see chapters 8 & 9 of ref. 28), or mixtures thereof. The salts can take any suitable form (e.g. gel, crystalline, amorphous, etc.), with adsorption of antigen to the salt being preferred. The concentration of $Al^{+++}$ in a composition for administration to a subject is preferably less than 5 mg/ml e.g. ≤4 mg/ml, ≤3 mg/ml, ≤2 mg/ml, ≤1 mg/ml, etc. A preferred range is between 0.3 and 1mg/ml. A maximum of 0.85 mg/dose is preferred. Aluminium hydroxide and aluminium phosphate adjuvants are particularly suitable for use with the invention.

Compositions may include an antimicrobial, particularly when packaged in multiple dose format. Antimicrobials such as thiomersal and 2-phenoxyethanol are commonly found in vaccines, but it is preferred to use either a mercury-free preservative or no preservative at all. The composition is preferably free of thiomersal.

Compositions may comprise detergent e.g. a Tween (polysorbate), such as Tween 80. Detergents are generally present at low levels e.g. <0.01% (v/v). Compositions may include residual detergent (e.g. deoxycholate) from OMV preparation. The amount of residual detergent is preferably less than 0.4 μg (more preferably less than 0.2 μg) for every μg of meningococcal protein.

If a vaccine includes lipooligosaccharides (LOS), the amount of LOS is preferably less than 0.12 μg (more preferably less than 0.05 μg) for every μg of protein.

Compositions may include sodium salts (e.g. sodium chloride) to give tonicity. A concentration of 10±2 mg/ml NaCl is typical e.g. about 9 mg/ml.

Vaccine Efficacy

Compositions for use in the present invention preferably have a vaccine efficacy against *N. gonorrhoeae* of at least 10% e.g. ≥20%, ≥30%, ≥40%, ≥50%, ≥60%, ≥70%, ≥80%, ≥85%, ≥90%, or more. As explained in reference [11], vaccination against gonorrhoea may be cost-effective even at a vaccine efficacy against *N. gonorrhoeae* as low as 20% (10% with a substantial increase in antibiotic resistant strains of *N. gonorrhoeae*).

Vaccine efficacy is determined by the reduction in relative risk of developing gonococcal disease in subjects who receive a composition according to the invention compared to subjects who do not receive such a composition (e.g. are non-immunized or who receive a placebo or negative control). Thus the incidence of gonococcal disease in a population which has been immunized according to the invention (e.g. 0.67% incidence) is compared to the incidence in a control population who has not been immunized according to the invention (e.g. 4.73% incidence) to give relative risk (e.g. 0.67/4.73=14%) and vaccine efficacy is 100% minus this figure (e.g. 86% efficacy).

Vaccine efficacy is determined for a population rather than for an individual. Thus it is a useful epidemiologic tool but does not predict individual protection. For instance, an individual subject might be exposed to a very large inoculum of the infecting agent, or might have other risk factors which make them more subject to infection, but this does not negate the validity or utility of the efficacy measure. The size of a population which is immunized according to the invention, and for which vaccine efficacy is measured, is ideally at least 100 and may be higher e.g. at least 500 subjects. The size of the control group should also be at least 100 e.g. at least 500.

Administration of the Composition

Compositions of the invention will generally be administered directly to a subject. Direct delivery may be accomplished by parenteral injection (e.g. subcutaneously, intraperitoneally, intravenously, intramuscularly, or to the interstitial space of a tissue), or by any other suitable route. Intramuscular administration is preferred e.g. to the thigh or the upper arm. Injection may be via a needle (e.g. a hypodermic needle), but needle-free injection may alternatively be used. A typical intramuscular dosage volume is 0.5 ml.

As used herein, a 'dose' of the composition is a volume of the composition suitable for administration to a subject as a single immunisation. Human vaccines are typically administered in a dosage volume of about 0.5 ml, although fractional doses may be administered (e.g., to children). The volume of the dose may further vary depending on the concentration of the antigens in the composition.

The composition may further be provided in a 'multidose' kit, i.e., a single container containing sufficient composition for multiple immunisations. Multidoses may include a preservative, or the multidose container may have an aseptic adaptor for removal of individual doses of the composition.

Administration can involve a single dose schedule, but will usually involve a multiple dose schedule. Preferably, a schedule of at least three doses is given. Suitable intervals between priming doses can be routinely determined e.g. between 4-16 weeks, such as one month or two months.

The subject who is immunized is a human being, who may be any age e.g. 0-12 months old, 1-5 years old, 5-18 years old, 18-55 years old, or more than 55 years old. Preferably, the subject who is immunized is a human adolescent (e.g. 12-18 years old) or an adult (18 years or older).

Optionally, the subject is an adolescent or adult who has been immunized against *N. meningitidis* in childhood (e.g. before 12 years of age), and who receives a booster dose of an immunogenic composition according to the invention to protect against *N. gonorrhoeae*.

In a preferred embodiment, the subject who is immunized is at increased risk of infection with *N. gonorrhoeae* (e.g. at increased risk relative to the average risk in the general population). Such subjects may include (but are not limited to) those who are sexually active; those with multiple sexual partners (e.g. including sex workers); men who have sex with men (MSM); subjects with a partner who has tested positive for *N. gonorrhoeae*; military personnel; neonates/infants whose mother was positive for *N. gonorrhoeae* at birth (to protect against vertical transmission during delivery); and/or illegal drug users (reference 29 links illegal drug use before or during sex to increased risk of gonorrhoea).

In some embodiments, the subject who is immunized is already seropositive for *N. gonorrhoeae*. Recovery from infection with *N. gonorrhoeae* does not confer immunity against re-infection, and individuals may become infected multiple times, even with the same strain. Therefore, immunization of subjects seropositive for *N. gonorrhoeae* is of interest, for example to reduce the risk of re-infection.

Optionally, a subject who is immunized according to the invention is co-immunized against one or more additional sexually-transmitted infections, for example infections and/or diseases caused by human papillomavirus (HPV), hepatitis A virus, hepatitis B virus, human immunodeficiency virus (HIV), herpes simplex virus (HSV), *Chlamydia trachomatis* and/or Zika virus. In a preferred embodiment, the subject is co-immunized against *N. gonorrhoeae* and HPV. This embodiment is particularly preferred for immunization of adolescents, especially adolescent females. Preferably, the subject is immunized against HPV types 16 and 18 (e.g.

using the CERVARIX® vaccine). Optionally the subject is also immunized against HPV types 6 and 11 (e.g. using the GARDASIL® vaccine). The subject may also be immunized against HPV types 31, 33, 45, 52 and 58 (e.g. using the GARDASIL® 9 vaccine). Such a co-immunization strategy is particularly suitable for adolescent subjects.

Where the invention refers to co-immunization, the different immunogenic compositions/vaccines can be administered either separately or as a combination.

Where the vaccines are administered separately, they will typically be administered at different sites e.g. one vaccine to the left upper arm, and a second vaccine to the right upper arm. Thus two vaccines may be administered contralaterally (e.g. both arms, or both legs, or a contralateral arm and leg) or ipsilaterally (e.g. the arm and leg on the same side of the body). Although the vaccines are administered separately, they are administered at substantially the same time (e.g. during the same medical consultation or visit to a healthcare professional or vaccination centre), such as within 1 hour of each other.

Rather than co-immunising separately, however, administration as a combination may be performed.

Thus co-immunisation may use a combination vaccine i.e. a single composition in which the different immunogens are admixed. Combination vaccines offer subjects the advantage of receiving a reduced number of injections, which can lead to the clinical advantage of increased compliance.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 30-36, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

Where the invention concerns an "epitope", this epitope may be a B-cell epitope and/or a T-cell epitope, but will usually be a B-cell epitope. Such epitopes can be identified empirically (e.g. using PEPSCAN [37,38] or similar methods), or they can be predicted (e.g. using the Jameson-Wolf antigenic index [39], matrix-based approaches [40], MAP-ITOPE [41], TEPITOPE [42,43], neural networks [44], OptiMer & EpiMer [45, 46], ADEPT [47], Tsites [48], hydrophilicity [49], antigenic index [50] or the methods disclosed in references 51-55, etc.). Epitopes are the parts of an antigen that are recognized by and bind to the antigen binding sites of antibodies or T-cell receptors, and they may also be referred to as "antigenic determinants".

References to a percentage sequence identity between two amino acid sequences means that, when aligned, that percentage of amino acids are the same in comparing the two sequences. This alignment and % homology or sequence identity can be determined using software programs known in the art, for example those described in section 7.7.18 of ref. 56. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 57.

The word "substantially" does not exclude "completely" e.g. a composition which is "substantially free" from Y may be completely free from Y. Where necessary, the word "substantially" may be omitted from the definition of the invention.

BRIEF DESCRIPTION OF DRAWINGS

FIG. 9—Graphs showing that OMVnz induces a T cell response with a Th1/Th17 profile (FIGS. 9A, 9B, 9C, 9D and 9E).

MODES FOR CARRYING OUT THE INVENTION

Example 1—Ecological Analysis

Figure 1:
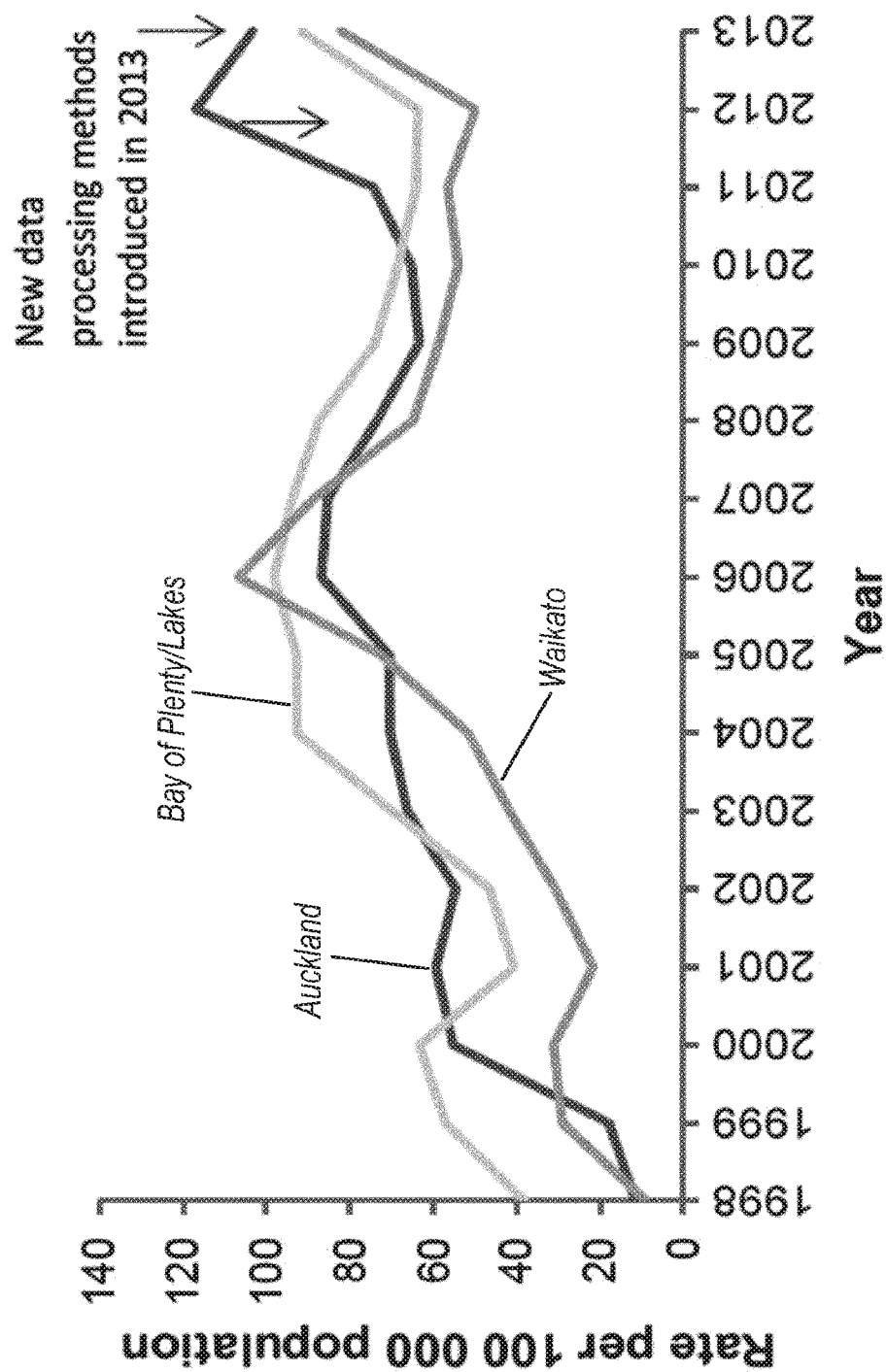
FIG. 1—Gonorrhoea rates in selected regions of New Zealand, 1998-2013. Adapted from reference 59.

Observational data in New Zealand suggested a possible effect of outer membrane vesicle (OMV) meningococcal group B vaccines on gonorrhoea incidence.

Due to an epidemic of serogroup B meningococcal disease, caused by a single clone expressing the P1.7-2,4 PorA protein, a vaccine based on the Norwegian MenBvac was developed for New Zealand (MeNZB™). The NZ McNZB™ campaign began in the Northern region in the second half of 2004. Prior to that 1,278 persons received the vaccine as part of the phase I and II clinical trials. The programme then extended beyond the northern region in 2005. By end of June 2006 coverage of three doses for children was 80% for three doses, around 85% for those aged 15-17 years and for 18- to 19-year-olds around 50%. The vaccine was then offered as a special schedule for infants until 2008 when it was withdrawn. Vaccine administered to cohorts born in 1984-1998 occurred between 2004 and 2006. Between 2004-2008 rates of partial vaccination (<3 doses) amongst those aged 0-19 years ranged from 3.1 up to 22.3% in 2005.

In NZ, surveillance of gonorrhoea is done by laboratory notification and collected by the Institute of Environmental Science and Research (ESR). Recent surveillance indicates stable rates of reporting from 2009 to 2011. An increase in 2012 may be as a result of the introduction of nucleic acid amplification testing (NAAT). There were 3,344 laboratory confirmed cases in 2013. Gonorrhoea is not a notifiable disease in NZ.

There was a long-term upward trend for gonorrhoea rates between 1998 and 2006, followed by a steady decline. Gonorrhoea rates reported by family planning clinics, sexual health clinics and student & youth health clinics increased during 2005-2009. However, from 2006-2009, the restricted national estimate based on laboratory testing indicated a decrease of 22% [58]. From 2012 to 2013 rates increased in two major regions but decreased in the Auckland region.

In 2013, the mean age of laboratory confirmed cases was 24.8 years and 59% were aged 15-24 years. The highest rate occurred in the 15-19 year age group.

While there has been a recent increase in rates from 2009 to 2013, a reduction can be observed in the 15- to 19-year-old females, from 2009 to 2011, before a sharp increase (43%) occurred. New data processing methods may confound. From 2004-2008, clinic reported rates of gonorrhoea increased more for males (31.6%) than females (19.5%) [58].

Gonorrhoea rates vary considerably by region throughout NZ with the highest reported rates occurring in Tairawhiti District Health Board 400 per 100,000 compared to 12 or less per 100,000 in South Canterbury, Taranaki and Nelson-Marlborough.

The gonorrhoea data in NZ suggest a potential weak ecological pattern of decline in gonorrhoea cases following the widespread use of an OMV vaccine (FIG. 1).

Example 2—Retrospective Case Control Study

The vaccine effectiveness (VE) of an OMV meningococcal B vaccine (MeNZB™) against gonorrhoea cases among young adults 15-30 years or age was evaluated, to test the hypothesis that exposure to the McNZB™ vaccine is associated with a reduction in risk for gonorrhoea.

Methods

A retrospective case-control study was conducted using sexual health clinic data to estimate VE of the McNZB™ vaccine against gonorrhoea by comparing proportions of vaccinated versus unvaccinated individuals in the case group (laboratory confirmed gonorrhoea only) against the control group (laboratory confirmed *chlamydia* only). Demographic data, sexual health clinic data and the National Immunisation Register were linked using a unique personal identifier. For primary analysis, cases were confirmed by laboratory isolation or detection of *N. gonorrhoeae* from a clinical specimen; controls were individuals with a positive *chlamydia* test. An odds ratio was estimated using conditional logistic regression. VE as a percent was calculated as 100*(1-Odds Ratio).

The study population consisted of all those aged 15-30 years (born between 1984 and 1998) attending Sexual Health Clinics (SHC) who were diagnosed with gonorrhoea, *chlamydia* or both and eligible to receive the McNZB™ vaccine in New Zealand between 2004 and 2008, which was delivered though schools and primary health care.

Data sources were the NZ National Health Index (NHI), which contains demographic information for anyone using the NZ health system, and the National Immunisation Register (NIR), which includes all individuals who received McNZB™ vaccinations from 2004. These datasets use the unique NHI number, a person-specific alphanumeric identifier, which enabled data linkage.

SHCs provided the NHI numbers associated with all *chlamydia* and gonorrhoea infections diagnosed by their clinics from January 2004 to January 2016 for linkage to the NIR and NHI datasets.

During the study period all SHCs routinely tested for both gonorrhoea and *chlamydia* by culture or, more recently, Nucleic Acid Amplification Techniques (NAAT). Each positive case was assigned a unique identifier for sexually transmitted infection (STI) surveillance purposes. Historically, identifiers were clinic-determined for confidentiality but, more recently, there has been greater use of NHI number identifiers with NHI number recorded for around 60% of reported gonorrhoea cases from 2010 onwards. For non-NHI identified cases during the study period, the unique clinic identifier was mapped to the person's NHI number using clinics' electronic patient databases or manually from paper records. The number of cases and controls in any one year by each SHC were validated against data reported to the national coordinating centre for STI surveillance in the same year.

For primary analysis, cases were defined as gonorrhoea positive and controls as *chlamydia* positive. Individuals with co-infection of gonorrhoea and *chlamydia* were excluded. However, because co-infected individuals can also be considered as cases, controls or as a different disease, sensitivity analyses were conducted to see how much a change in classification and inclusion of the co-infected individuals affects the VE estimate.

NZ recorded *chlamydia* rates of 633 cases per 100,000 population are eight times that of gonorrhoea, 78 cases per 100,000, in 2013 [59]. A sample size of 1,300 cases provides 80% power at alpha=0.05 for a possible VE of 20% or higher for vaccination coverage up to 80%.

Analyses were conducted using unconditional logistic regression including age group, ethnicity, gender, geographic location and deprivation quintile to provide an adjusted estimate of VE. Cases or controls with missing data ethnicity or deprivation data were excluded. An odds ratio was estimated using conditional logistic regression by SAS Enterprise Guide 6.1. VE as a percent was then calculated as 100*(1-Odds Ratio).

Further sensitivity analyses were undertaken to explore assumptions:

Firstly there is a lack of precision around the time of infection and time to diagnosis as well as a lack of precision about when immunity might occur following vaccination. Therefore, three separate analyses were conducted, assuming three different points in time after the third dose of McNZB™ at which an individual was considered to be immunized: one; three; and six months.

To estimate duration of VE, the data were analysed grouped by time since vaccination, with cases and controls occurring in the years during and immediately following the vaccination programme in 2004-2009 analysed separately from the more distal cases and controls (2010-2014).

Results

There were 14,730 cases and controls for analyses from eleven participating sexual health clinics consisting of 1,241 incidences of gonorrhoea, 12,487 incidences of *chlamydia* and 1,002 incidences of *chlamydia* co-infection. Vaccinated individuals were significantly less likely to be cases (Adjusted OR 0.69 (95% CI 0.61-0.79). The VE estimate for the McNZB™ vaccine against gonorrhoea after adjustment for ethnicity, deprivation, geographic area and gender was 31% (95% CI 21-39).

Participating Sexual Health Clinics

There were eleven participating clinics from nine District Health Boards in six diverse geographical regions covering 2,998,941 from the total NZ population of 4,680,666 (56%).

Participants

SHCs provided details of 1,759 confirmed incidences of gonorrhoea, 15,090 confirmed incidences of *chlamydia* and 1,329 incidences of confirmed *chlamydia* and gonorrhoea co-infection among 15,067 attendees.

Repeat incidences of disease per individual were removed. Excluded because of incomplete information were three cases, four co-infections and 36 controls due to missing information about deprivation; eleven cases, 13 co-infected individuals and 269 controls with missing information about ethnicity; one control due to missing deprivation and ethnicity. The number of partially vaccinated individuals varied slightly with time since vaccination used in our analysis (Table 1).

Ethnic proportions of gonorrhoea-only and *chlamydia*-only cases were similar, with over 40% in each group being NZ European and over 30% Māori, followed by Pacific and Asian. However, co-infected cases were 50% Māori, with Pacific and European/other contributing less than 30% respectively (Table 1).

TABLE 1

Demographic characteristics of participants

| | Cases | Controls | | |
|---|---|---|---|---|
| | Gonorrhoea only | Co-infected | Chlamydia only | Total |
| Gender | | | | |
| Female | 483 (39%) | 562 (56%) | 7,092 (57%) | 8,137 |
| Male | 758 (61%) | 440 (44%) | 5,395 (43%) | 6,593 |
| Ethnicity | | | | |
| NZ European & Other | 516 (42%) | 200 (20%) | 5,780 (46%) | 6,496 |
| Māori | 467 (38%) | 511 (51%) | 4,325 (35%) | 5,303 |
| Pacific peoples | 188 (15%) | 262 (26%) | 1,870 (15%) | 2,320 |
| Asian | 70 (6%) | 29 (3%) | 512 (4%) | 611 |
| Deprivation | | | | |
| Low 1-2 | 101 (8%) | 38 (4%) | 1,199 (10%) | 1,338 |
| 3-4 | 125 (10%) | 79 (8%) | 1,570 (13%) | 1,774 |
| 5-6 | 207 (17%) | 99 (10%) | 2,114 (17%) | 2,420 |
| 7-8 | 298 (24%) | 238 (24%) | 3,001 (24%) | 3,537 |
| High 9-10 | 510 (41%) | 548 (55%) | 4,603 (37%) | 5,661 |
| Age Group | | | | |
| 15-19 years | 441 (36%) | 425 (49%) | 4,514 (42%) | 6,008 |
| 20-24 years | 613 (49%) | 351 (40%) | 4,899 (45%) | 6,779 |
| 25-30 years | 187 (15%) | 91 (10%) | 1,420 (13%) | 1,943 |

TABLE 1-continued

Demographic characteristics of participants

| | Cases | Controls | | |
|---|---|---|---|---|
| | Gonorrhoea only | Co-infected | Chlamydia only | Total |
| Vaccination | | | | |
| No | 632 (51%) | 419 (42%) | 5,310 (43%) | 6,361 |
| Partial | 98 (8%) | 89 (9%) | 753 (6%) | 940 |
| Yes | 511 (41%) | 494 (49%) | 6,424 (51%) | 7,429 |
| Total | 1,241 | 1,002 | 12,487 | 14,730 |

Vaccine coverage of the study population by each birth year and location was not available. However, coverage for 5-17-year-olds (those born 1987-2001) who received three doses was estimated as 86%, and for those born 1984-1985 coverage was 54%.

Interactions between vaccination status and gender, and vaccination status and ethnicity were not significant.

Vaccine Effectiveness

The estimate for VE of the 3+0 McNZB™ immunisation series against confirmed cases of gonorrhoea among adolescents and adults aged 15-30 years based on the odds ratio is 31% (95% CI 21-39%). No significant effect of partial vaccination was measurable.

Varying the definition of cases to include co-infected as cases reduced the VE estimate. The OR was 0.77 (0.70-0.85) giving a VE of 23% (15-30%). Assigning co-infected to controls had a minor impact on the estimate of vaccine effectiveness, i.e. the effect remained significant and within a similar range, adjusted OR of 0.71 (0.63-0.81) and therefore a VE of 29% (19-37%).

As co-infected individuals are likely to be different both epidemiologically and immunologically we evaluated them separately against *chlamydia*-only controls with gonorrhoea only cases removed. Vaccine effectiveness against co-infection was 14% (1-26%).

The estimated VE for Maori was similar to that for the population as a whole at 31% (24-39%). We had insufficient power to explore other ethnicities. There was no significant difference by gender with VE in females 36% (22-48%) and males 35% (11-36%).

Shortening the length of time after the third vaccination date that we considered a person fully vaccinated decreased the estimate for VE slightly but not significantly (see Table 2).

TABLE 2

Crude and adjusted VE. Gonorrhea only as cases, chlamydia only as controls. Adjusted for age group, ethnicity, gender, geographic location and deprivation.

| Vaccination status (>6 months between 3rd dose and disease diagnosis) | Crude OR (95% CI) | Adjusted OR* (95% CI) | Vaccine Effectiveness (95% CI) |
|---|---|---|---|
| Vaccinated vs Unvaccinated | 0.67 (0.59-0.76) | 0.69 (0.61-0.79) | 31% (21-39) |
| Partial vs Unvaccinated | 1.1 (0.87-1.4) | 1.1 (0.86-1.4) | No significant effect |
| Gender | | | |
| Female vs Male | 0.49 (0.43-0.55) | 0.48 (0.42-0.54) | N/A |
| Ethnicity | | | |
| Asian vs European | 1.5 (1.2-2.0) | 1.3 (1.0-1.7) | N/A |
| Māori vs European | 1.2 (1.1-1.4) | 1.4 (1.2-1.6) | N/A |
| Pacific people vs European | 1.1 (0.95-1.3) | 0.96 (0.79-1.2) | N/A |

TABLE 2-continued

Crude and adjusted VE. Gonorrhea only as cases, chlamydia only as controls. Adjusted for age group, ethnicity, gender, geographic location and deprivation.

| Vaccination status (>6 months between 3rd dose and disease diagnosis) | Crude OR (95% CI) | Adjusted OR* (95% CI) | Vaccine Effectiveness (95% CI) |
|---|---|---|---|
| Deprivation | | | |
| Lowest (1-2) vs Highest (9-10) | 0.76 (0.61-0.95) | 0.70 (0.56-0.89) | N/A |
| 3-4 vs 9-10 | 0.72 (0.59-0.88) | 0.67 (0.54-0.83) | N/A |
| 5-6 vs 9-10 | 0.88 (0.75-1.0) | 0.85 (0.71-1.0) | N/A |
| 7-8 vs 9-10 | 0.90 (0.77-1.0) | 0.85 (0.73-0.99) | N/A |
| Age Group | | | |
| 15-19 vs 25-30 | 0.77 (0.64-0.92) | 1.1 (0.91-1.3) | N/A |
| 20-24 vs 25-30 | 0.94 (0.79-1.1) | 1.1 (0.89-1.3) | N/A |
| Location | | | |
| Region 1 vs Region 6 | 0.81 (0.66-0.99) | 0.81 (0.66-0.99) | N/A |
| Region 2 vs Region 6 | 0.78 (0.60-1.0) | 0.80 (0.62-1.0) | N/A |
| Region 3 vs Region 6 | 0.22 (0.14-0.39) | 0.23 (0.14-0.37) | N/A |
| Region 4 vs Region 6 | 0.82 (0.64-1.1) | 0.97 (0.75-1.3) | N/A |
| Region 5 vs Region 6 | 0.54 (0.43-0.68) | 0.51 (0.40-0.64) | N/A |
| Sensitivity analysis results | | | |
| Vaccinated vs Unvaccinated (>3 months between 3rd dose and disease diagnosis) | 0.80 (0.73-0.88) | 0.71 (0.62-0.80)* | 29% (20-38) |
| Vaccinated vs Unvaccinated (>1 month between 3rd dose and disease diagnosis) | 0.68 (0.60-0.77) | 0.71 (0.62-0.80)* | 29% (20-38) |

Figure 2:
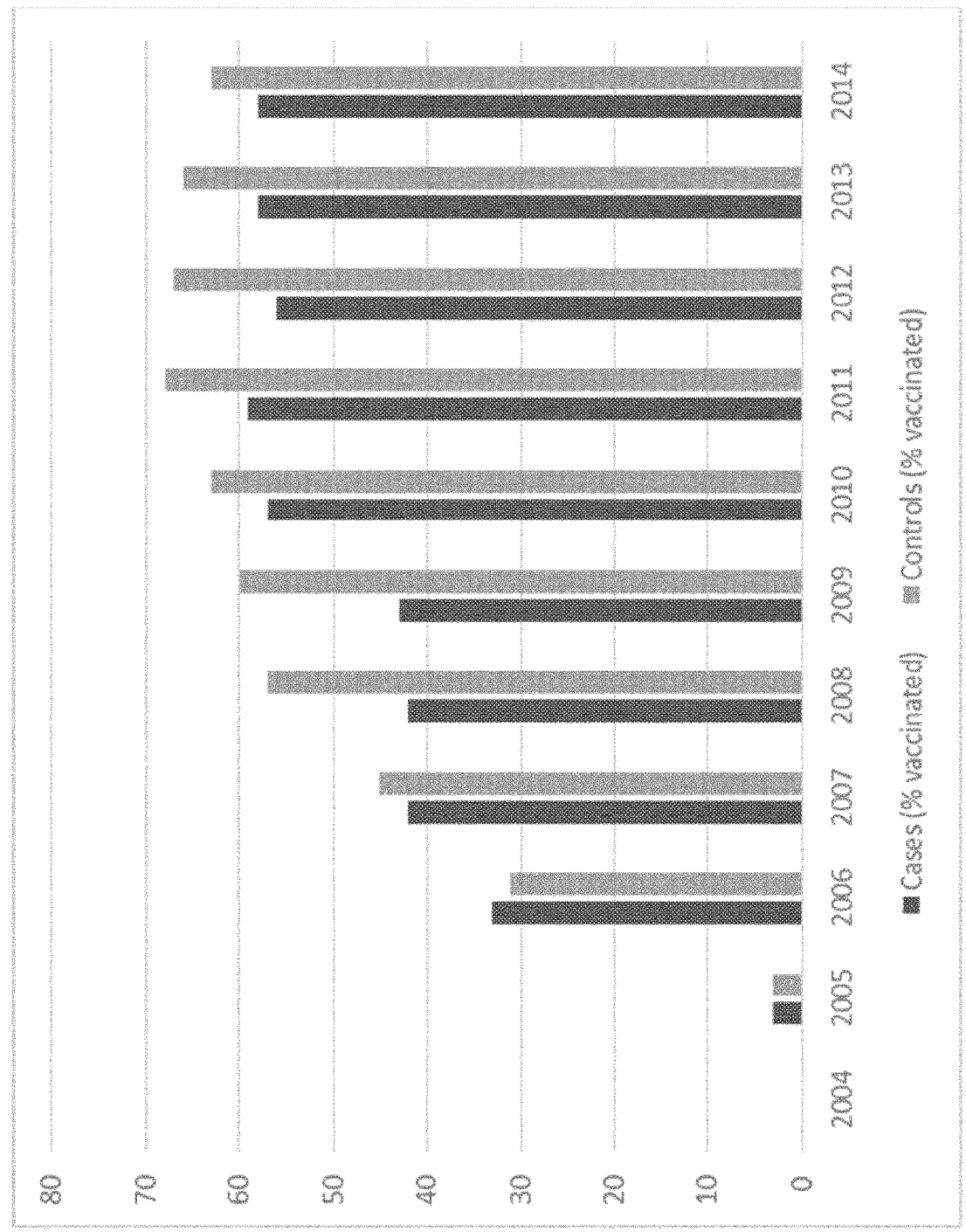
FIG. 2—Year by year difference in the proportion vaccinated for cases and controls. The difference in height between each pair of columns is the unadjusted estimate of the effect of the vaccine for each year.

*After adjustment for ethnicity, gender, age group, deprivation and geographical location Duration of Protection Analysing cases and controls as two separate groups according to time since vaccination showed a stronger VE estimate in the years during and immediately following the vaccination programme (2004-2009), 20% (2-34) compared to more recent disease diagnosis (2010-2014), 9% (0-25%). This waning effect is also evident when looking at the difference in proportion of cases versus control vaccinated by year (see Table 3 and FIG. 2).

CONCLUSION

Prior exposure to McNZB™ vaccine in SHC attendees was associated with a significant protective effect against gonorrhoea. This effect remained robust throughout multiple sensitivity analyses. Examination of time from vaccination to diagnosis indicated a waning of effect. Less time since vaccination was associated with a greater protective effect. Co-infection with *chlamydia* was associated with lower VE.

TABLE 3

Odds Ratios for gonorrhea by ethnicity, gender, deprivation and age among visitors to participating SHCs with partially vaccinated excluded

| | Crude OR (95% CI) | Adjusted OR* (95% CI) | Vaccine Effectiveness (95% CI) |
|---|---|---|---|
| Cases are gonorrhea and controls chlamydia (co-infected excluded) | | | |
| Vaccinated vs Unvaccinated 2004-2014 | 0.65 (0.57-0.72) | 0.69 (0.61-0.79) | 31% (21-39) |
| Vaccinated vs Unvaccinated 2004-2009 | 0.74 (0.61-0.89) | 0.80 (0.66-0.98) | 20% (2-34) |
| Vaccinated vs Unvaccinated 2010-2014 | 0.72 (0.61-0.86) | 0.91 (0.75-1.1) | 9% (0-25) |
| Cases are gonorrhea, controls are co-infected and chlamydia | | | |
| Vaccinated vs Unvaccinated 2004-2014 | 0.67 (0.59-0.76) | 0.71 (0.63-0.81) | 29% (19-37) |
| Vaccinated vs Unvaccinated 2004-2009 | 0.75 (0.62-0.90) | 0.83 (0.68-1.0) | 17% (0-32) |
| Vaccinated vs Unvaccinated 2010-2014 | 0.71 (0.60-0.85) | 0.91 (0.75-1.1) | 9% (0-25) |
| Cases are gonorrhea and co-infected, controls chlamydia | | | |
| Vaccinated vs Unvaccinated 2004-2014 | 0.79 (0.72-0.87) | 0.77 (0.70-0.85) | 23% (15-30) |
| Vaccinated vs Unvaccinated 2004-2009 | 0.75 (0.65-0.87) | 0.76 (0.65-0.89) | 24% (11-35) |
| Vaccinated vs Unvaccinated 2010-2014 | 0.92 (0.81-1.0) | 0.96 (0.84-1.1) | 4% (0-16) |
| Cases are co-infected, controls chlamydia only (gonorrhea only excluded) | | | |
| Vaccinated vs Unvaccinated 2004-2014 | 0.98 (0.85-1.1) | 0.86 (0.74-0.99) | 14% (1-26) |
| Vaccinated vs Unvaccinated 2004-2009 | 0.78 (0.62-0.97) | 0.69 (0.55-0.88) | 31% (12-45) |
| Vaccinated vs Unvaccinated 2010-2014 | 1.2 (1.0-1.5) | 1.0 (0.81-1.3) | 0% (0-19) |

*After adjustment for ethnicity, gender, age, deprivation and geographical location This is the first time a vaccine has demonstrated any protection against gonorrhoea.

This study provides a rationale for the use of meningococcal OMVs in immunizing against *N. gonorrhoeae*.

Reports on the duration of protection afforded by OMV vaccines against meningococcal disease vary by age and population, but serum bactericidal activity has typically diminished among a significant proportion of vaccines by two years [60]. As protection against meningococcal disease is dependent on the presence of functional antibody, due to the rapidity of overwhelming infection, immunological memory is presumably less relevant. In contrast, gonorrhoea follows a different disease process. Infection may be present for months before diagnosis, or even subclinical. We found the VE estimate fell as the time following the vaccination programme grew, supporting a waning of vaccine effect over time.

Ethnic proportions for either gonorrhoea or *chlamydia* alone were the same, both dominated by NZ European. In contrast the highest proportion of co-infected were Māori. Although this study was underpowered to explore ethnicity, it is possible that if the vaccine was more effective in Māori, and more effective against gonorrhoea-only infected, then proportionally more cases of gonorrhoea were prevented in the gonorrhoea-only group among Māori. A more limited effect against gonorrhoea in the presence of *chlamydia* may have mitigated advantage by ethnicity.

A major strength of this study was the ability to robustly link data using the unique NHI number. All individuals receiving a dose of McNZB™ were recorded in the NIR, enabling population data linkage of McNZB™ vaccination with confirmed cases of gonorrhoea and controls in the period post-vaccination.

Sensitivity analyses were used to explore any impact of various assumptions in the construction of the variable categories on the effectiveness estimate. One issue was that co-infected individuals could be assigned as either cases or controls. Therefore, additional analyses were conducted, varying the classification of co-infected individuals. This decreased the estimate of effectiveness but not significantly. However, analysis of gonorrhoea-only and co-infected individuals as two distinct conditions suggests that vaccine effectiveness is lower when gonorrhoea is complicated by co-infection with *chlamydia*.

Co-infection with *C. trachomatis* and *N. gonorrhoeae* is common yet interactions between the two organisms have received little attention. Estimates of co-infection rates vary widely. A cross-sectional study in the UK estimated 24% of heterosexual men and 39% of women presenting to a sexual health service with gonorrhoea were co-infected, being more likely in younger people [61]. The proportion of gonorrhoea cases also testing positive for *chlamydia* in NZ is estimated to be 42%, with previous estimates ranging from 35-41% (see references 61 and 62). Estimates of gonorrhoea positivity amongst NZ *chlamydia* cases range from 13-20% [61]. In the current study population nearly half of gonorrhoea cases were co-infected.

Co-infection may favour the proliferation of gonococci [63], effectively by providing them more host cells. In some women, co-infection has been associated with significant elevations of cytokines (IL-1, 1-6, IL-8 and IL-10). While cytokines in genital secretions from women with gonorrhoea are not elevated compared with uninfected women, serum IL-6 is higher in infected women. However, concomitant infection with either *Trichomonas vaginalis* or *C. trachomatis* is associated with significantly elevated serum IL-1, IL-6 and IL-10 levels. Despite this, concomitant infection is not associated with higher gonococcal antibody concentrations in either serum or genital secretions [64]. It is clear that co-infection induces an immunological environment profoundly different to that present during infection with gonorrhoea alone, which may help explain the finding in this study that co-infection with *chlamydia* was associated with lower VE.

The retrospective nature of the study means the consistency of data collection over time within a single SHC or between SHCs could not be verified. To maximize consistency, long-standing case definitions were used, to reflect those used for routine STI surveillance in NZ, and the clinics' supplied data was verified with that received by the national STI surveillance co-ordinating centre.

The findings may not be generalizable to the wider population. Not all gonorrhoea cases present to SHCs; many people will consult their family physician. In addition, there is limited access to SHCs outside of larger NZ cities. The study population of SHC attendees may differ in age, ethnicity and socioeconomic variables, as well as sexual behaviour and past STI history [65]. However, the study population is likely to be at higher risk for STIs and co-infection, and so the study may have underestimated the possible effect of the vaccine in the wider population.

An effect of a meningococcal group B OMV vaccine was observed on a related organism which has a very different mode of infection and clinical presentation, and which has thus far eluded efforts to develop an effective prophylactic vaccine. The potential ability of a group B meningococcal vaccine to provide even modest protection against gonorrhoea will have significant public health benefits given the prevalence of gonorrhoea. This is of even greater importance given the increase in antibiotic resistance. In addition, if some degree of cross protection is observed then the findings can inform gonorrhoea vaccine development.

Example 3—OMVnz Antigens Induce Antibodies that are Bactericidal Against FA1090

Animals and Immunization Protocol

Six-week-old female CD1 mice (10 animals/group) were immunized with 10 μg of OMVnz antigen in combination with an alum adjuvant intraperitoneally on day 1, 21 and 35. Adjuvant alone, and an unrelated antigen (protein F from respiratory syncytial virus RSV), were used as negative controls. Sera samples were collected before the first immunization and two weeks after the last dose and used for serological analysis. Spleens were collected two weeks after the last dose to characterize the vaccine-induced T-cell responses.

Bactericidal Activity

Gonococcus strain FA1090 was grown in GC medium supplemented with 1% isovitalex for 1.5 hrs from $O.D._{600} \cong 0.1$ up to $O.D._{600} \cong 0.3$. The bacteria were diluted with a suspension of sera in SBA buffer (dPBS, 0.1% glucose, 1% BSA) and incubated for 1 hr at 37° C. with sera to be tested in the presence of human serum as exogenous complement source (16% v/v). Bacteria were then plated on a GC+1% isovitalex-plate.

Colonies were counted after 18 hrs of growth at 37° C. in 5% $CO_2$.

Serum bactericidal titers were calculated as the reciprocal dilution resulting in 50% killing with respect to the control (bacteria plus complement).

Results

Figure 3:
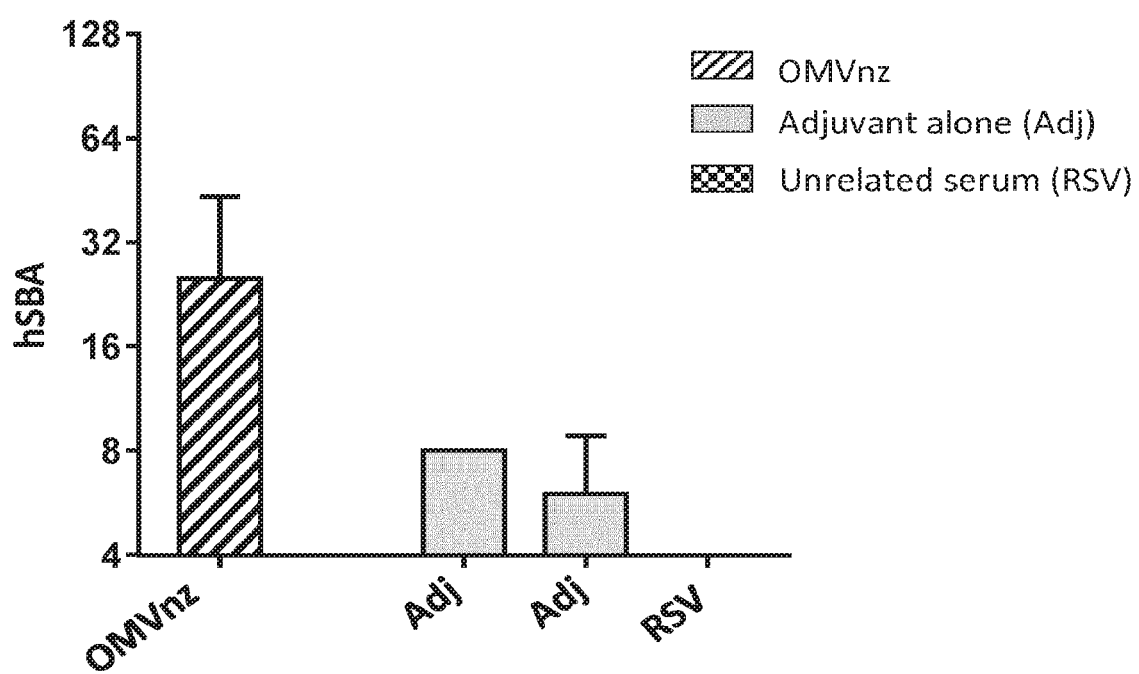
FIG. 3—SBA assay shows sera raised in mice against OMVnz induce bactericidal antibodies against N. gonorrhoeae FA1090.

As can be seen from FIG. 3, the hSBA titre of pool of sera from 10 mice immunized with OMVnz is high (≥16), showing bactericidal activity of sera raised against meningococcus B OMV against *N. gonorrhoeae*. In contrast, the titre of the adjuvant alone is low (≤8 in two different immunization schemes) and does not reach the threshold level for a statistically meaningful (i.e. non-background) titre for bactericidal activity. The measured hSBA titre for RSV is below 4 the lowest serum dilution tested, and is not shown on the graph. The bars represent the mean of at least two experiments.

Figure 4A:
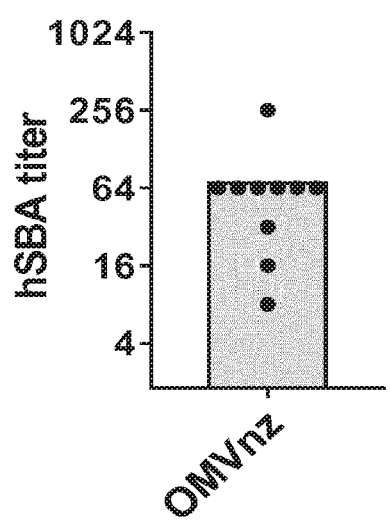
FIG. 4—SBA on single mice confirms pool analysis (FIGS. 4A and 4B).
Figure 4B:
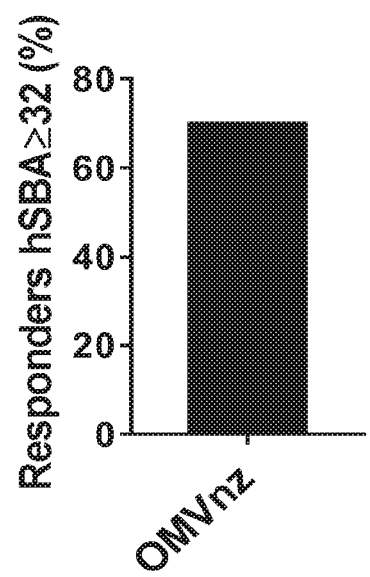

As shown in FIG. 4, the pool analysis of hSBA of sera from mice immunized with OMVnz in FIG. 3 is confirmed by considering hSBA for single mice within the pooled population. FIG. 4A plots the hSBA titre measured using the serum of each of the 10 immunized mice, with each dot representing the result for immune serum from an individual mouse. These data show that the OMVnz vaccine is able to induce a homogenous bactericidal response against *N. gonorrhoeae*. FIG. 4B shows that 70% of the mice immunized with OMVnz produced immune serum with a high hSBA titre of ≥32, indicating a strong bactericidal antibody response against *N. gonorrhoeae*.

Figure 5:
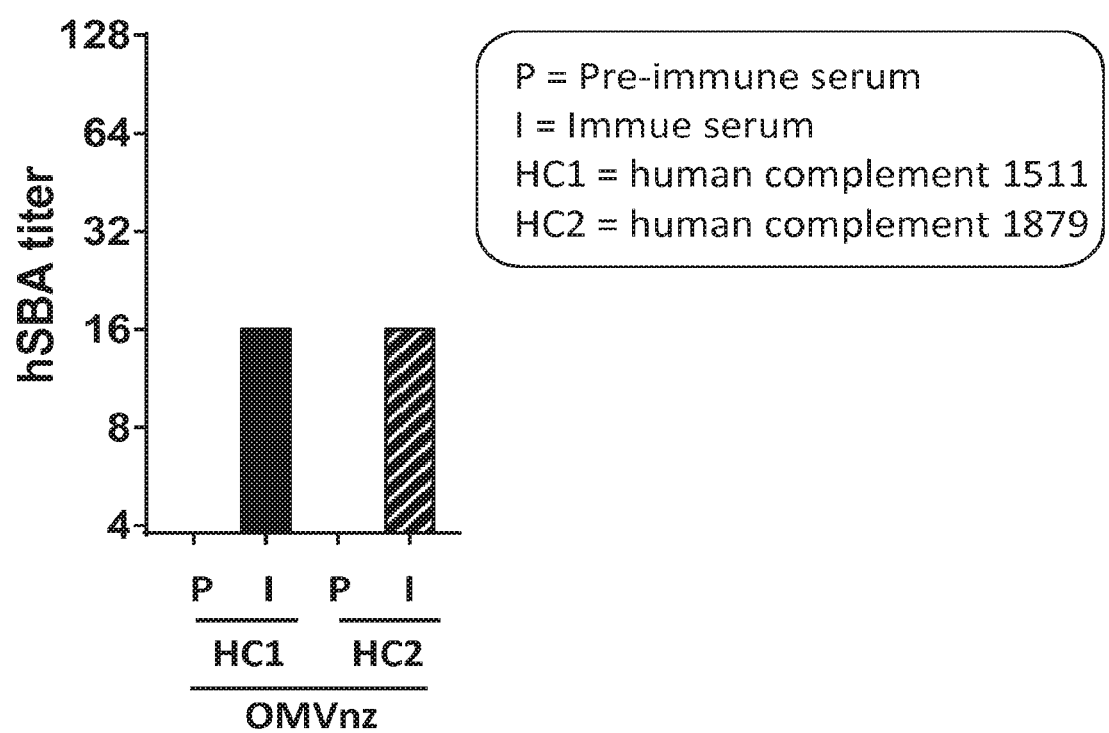
FIG. 5—Graph showing that results illustrated in FIGS. 3 and 4 are confirmed with different human complement lots (HC1511 and HC1879).

The positive results shown in FIG. 3 and FIG. 4 are further supported using different complement lots to reflect the variation in human complement, and these results are shown in FIG. 5. Two different human complement (HC) lots were tested—HC 1511 and HC 1879—using pre-immune (P) and immune (I) serum samples. In each hSBA assay, no result was observed using pre-immune serum (i.e. serum collected from the mice prior to immunization with OMVnz), whereas the SBA titre using immune serum (i.e. serum collected from the mice following immunization with OMVnz) was positive (a titre of 16) and consistent with both HC 1511 and HC 1879.

Competitive SBA

The results observed in the hSBA assays were reinforced by carrying out a competitive SBA assay to provide further indirect evidence of the immunogenic activity of OMVnz against *N. gonorrhoeae*.

Figure 6:
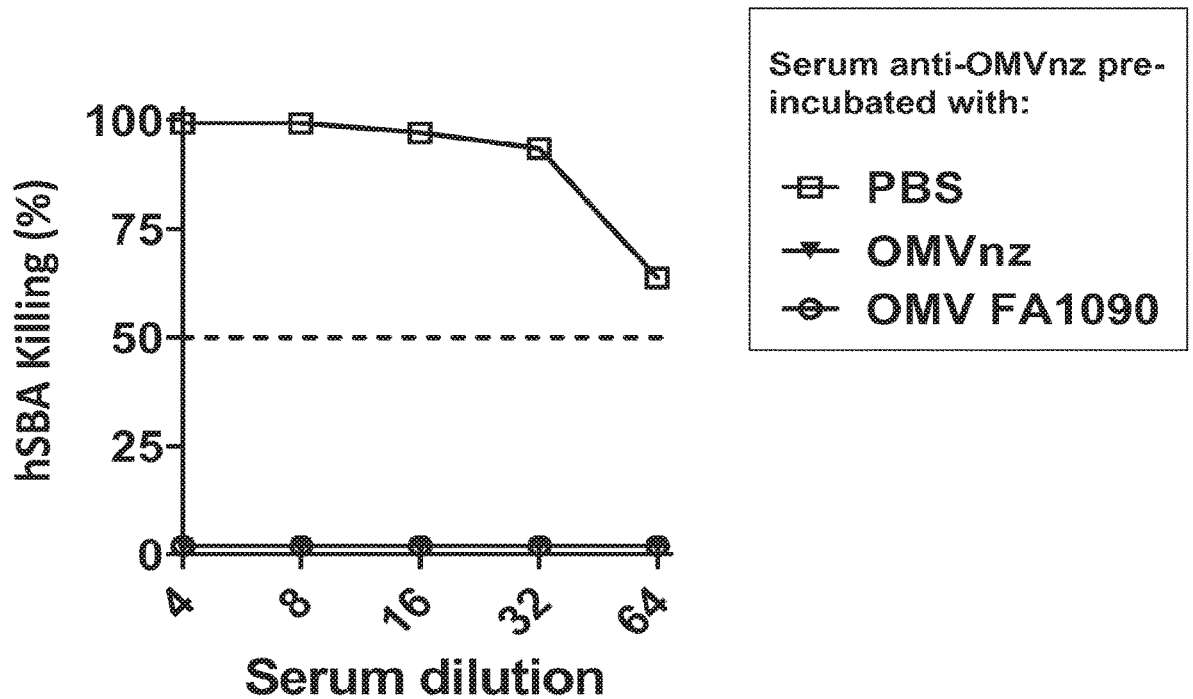
FIG. 6—Competitive hSBA indicates OMVnz induce bactericidal antibodies, and the SBA activity of anti-OMVnz serum is specific.

Sera from mice immunized with the immunogenic composition containing OMVnz was pre-incubated with either (i) OMVnz, (ii) PBS (phosphate-buffered saline) as a control, or (iii) OMV from gonococcal strain FA1090 as a further control, and subsequently incubated with target bacteria in the presence of human complement. Killing of the bacteria was then assessed, and the results are shown in FIG. 6.

As can be seen in the graph, killing was abolished when the immune sera was pre-incubated with OMVnz and OMV FA1090, because bactericidal antibodies in the recipients' sera bind to these OMV antigens during the pre-incubation phase and are therefore not available to bind to surface antigens on the bacteria. In contrast, pre-incubation with PBS has no effect on the bactericidal activity of immune sera, because PBS does not bind to the antibodies raised in the immune sera and said antibodies are therefore available to bind to the target bacterial surface antigens and initiate killing.

The competitive SBA results demonstrate the specificity of the bactericidal antibodies, validate the OMVnz SBA results described above and further support the immunogenicity of meningococcal OMV against *N. gonorrhoeae*.

Example 4—Sera Against OMVnz Reduces Adhesion of FA1090 to Human Cervical ME180 Cells In the absence of a suitable correlate of protection for gonorrhoea, the inventors performed a bacterial adhesion inhibition assay to test whether antibodies produced by OMVnz can prevent gonococci from adhering to cells of a human cervical cell line (ME180).

Bacteria from gonococcal strain FA1090 were labelled with a fluorescent dye (Oregon Green® 488, Thermofisher) and the labelled bacteria were pre-incubated for 1 hour with serially diluted sera obtained from mice immunized with OMVnz or pre-immune serum for 1 hour. Cells from human epithelial cervical cell line ME180 were then infected for 1 hour with bacteria+sera to allow for adhesion of the bacteria to the epithelial cells. In a final step, the plate was washed to remove unbound bacteria and fluorescent output was measured. Fluorescent output is proportional to bacterial adhesion to the epithelial cells, meaning that a decrease in fluorescence compare to control (bacteria plus cells without serum) corresponds to a decrease in adhesion of labelled gonococci to the cells.

Figure 7:
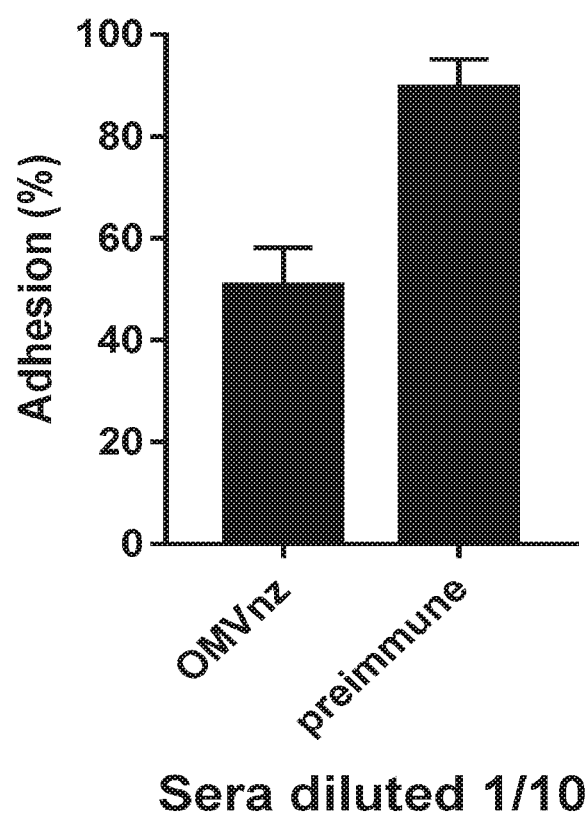
FIG. 7—Bacterial adhesion inhibition assay shows sera against OMVnz at high concentrations reduce adhesion of FA1090 to human cervical ME180 cells compared with control (bacteria plus cells without serum).

As shown in FIG. 7, sera against OMVnz at high concentration (1/10 dilution) reduces the adhesion of gonococcus FA1090 to human cervical ME180 cells, which is an interesting and important result in a clinical context. No significant reduction was observed in the pre-immune serum.

Example 5—OMVnz Induces a Cross-Reactive T-Cell Response with Th1 Profile

T-Cell Response Experimental Protocol

Mice were vaccinated with either an OMVnz vaccine adjuvanted with $Al(OH)_3$, or with the $Al(OH)_3$ adjuvant alone, at days 1, 22 and 36.

Splenocytes were isolated 2 weeks after the final vaccination, plated at $1-2\times10^6$ cells/well in 96-well plates, and stimulated with (i) OMV from gonococcus FA1090 strain or (ii) OMV from *Escherichia coli* (as a negative control) at final concentration of 10 µg/ml at 37° C. for 16-18 hrs in presence of anti-CD28 and anti-CD49d (2 µg/ml each, BD Biosciences) co-stimulatory molecules. Brefeldin A (5 µg/ml) is added for the last 4 h.

The cells were then stained with Live/Dead Yellow (Invitrogen), fixed and permeabilized with Cytofix/Cytoperm (BD Biosciences), washed in Perm/Wash buffer (BD Biosciences), incubated with anti-CD16/CD32 Fc block (BD Biosciences) for 20 min at room temperature, and then stained with fluorochrome-conjugated mAbs: anti-CD3-BV605, anti-CD4BV510, anti-IFN-γ-BV785, anti-IL-2-PE-Cy5, anti-TNF-Alexa488, anti-CD44-V450, anti-CD8-PE-CF594, anti-IL-17 PE-Cy7 and anti-IL-4-PerCPef710 and anti-IL-13-PerCPef710, in Perm/Wash buffer 1× (BD Biosciences) for 20 min at room temperature. Finally, the samples were washed twice in Perm/Wash buffer and suspended in PBS. Samples were acquired on LSRII flow cytometer (BD Biosciences) and analysed using FlowJo software (TreeStar).

Results

Figure 8:
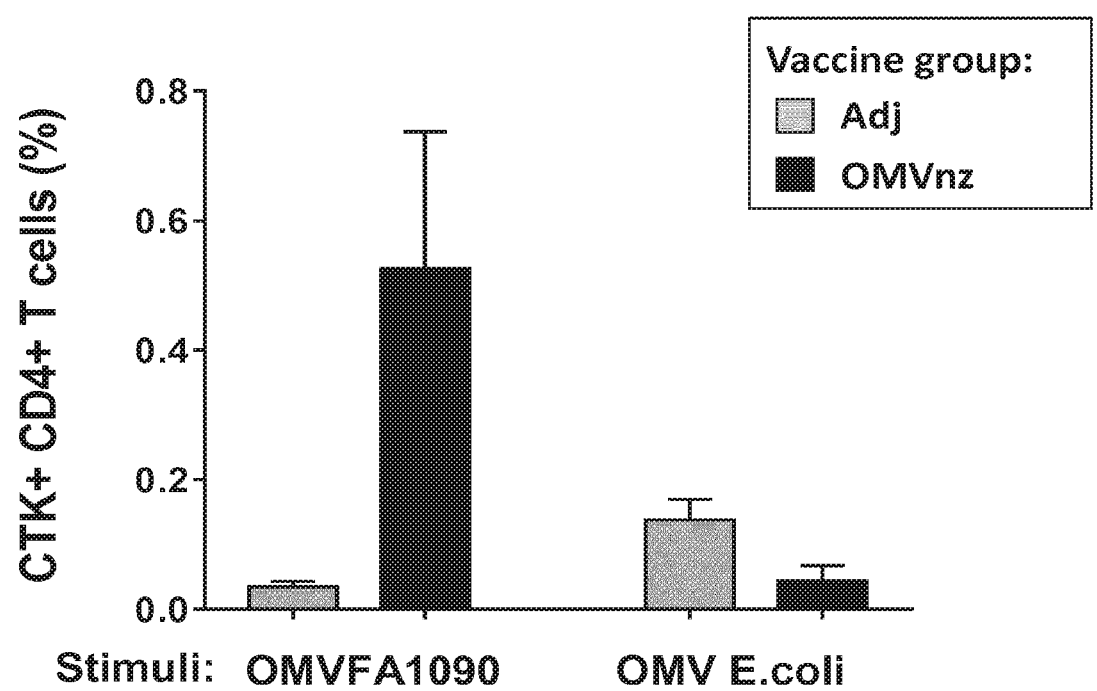
FIG. 8—Graph shows OMVnz induces a cross-reactive CD4+ T cell response against gonococcus strain FA1090.

As shown in FIG. 8, the OMVnz vaccine was able to induce a cross-reactive CD4+ T cell response against gonococcal antigen OMV FA1090. In contrast, the OMVnz vaccine was unable to induce a T cell response against the *E. coli* OMV antigen. Similarly, no significant CD4+ T cell response was raised against either the gonococcus or *E. coli* OMV antigens in the population immunized with the adjuvant alone.

This result indicated that the OMVnz vaccine was able to induce a T-cell responses against the gonococcal antigen, and so in order to understand the profile of the T-cell responses that was being raised the inventors studied different cytokines produced by vaccine-specific CD4+ T cells, which are known to be indicative of different T-cell responses profiles, as follows:

TNF and IL-2 are associated with a Th0 profile.
IL-17 is associated with a Th17 profile.
IL-4 and IL-13 are associated with a Th2 profile.
IFN-γ is associated with a Th1 profile.

FIG. 9 shows that the T-cell responses raised by the OMVnz vaccine against the gonococcal antigen exhibits Th1, Th17 and Th0 profiles, associated with the detection of cytokines IFN-γ (FIG. 9A), IL-17 (FIG. 9C) and IL-2 and TNF (FIGS. 9D and 9E) respectively. In agreement with these results, no significant level of IL-4 or IL-13 was detected (FIG. 9B). The Th1 profile is particularly interesting because this profile is thought to be associated with resistance to, and fast clearance of, gonococcus infection in the animal model.

It will be understood that the invention is described above by way of example only and modifications may be made whilst remaining within the scope and spirit of the invention.

REFERENCES

[1] Newman et al. (2015) *PloS one* 10:e0143304.
[2] Lewis (2014) *Curr. Opin. Infect. Dis.* 27:62-67.
[3] Bolan et al. (2012) *N. Engl. J. Med.* 366:485-487.
[4] Mehta et al. (2003) *Sexually transmitted infections* 79:124-128.
[5] Edwards et al. (2016) *Crit. Rev. Microbiol.* 1-14.
[6] Zhu et al. (2011) *Frontiers in Microbiology* 2:124.
[7] Jerse et al. (2014) *Vaccine* 32:1579-1587.
[8] Jerse et al. (2014) *Vaccine* 32:1579-87.
[9] Tinsley and Nassif (1996) *Proc. Natl. Acad. Sci. USA* 93:11109-11114.
[10] Muzzi et al. (2013) *mBio* 4:e00163-13
[11] Regnier and Huels (2014) *Hum. Vacc. Immunother.* 10:3737-3745
[12] WO02/09643.
[13] Katial et al. (2002) *Infect. Immun.* 70:702-707.
[14] U.S. Pat. No. 6,180,111.
[15] WO01/34642.
[16] WO2006/046143.
[17] WO2004/019977.
[18] European patent 0011243.
[19] Fredriksen et al. (1991) *NIPH Ann.* 14(2):67-80.
[20] WO01/91788.
[21] WO2005/004908.
[22] WO2011/036562.
[23] Claassen et al. (1996) *Vaccine* 14:1001-8.
[24] de Kleijn et al. (2000) *Vaccine* 18:1456-66.
[25] WO03/105890.
[26] WO2006/024946
[27] Gennaro (2000) *Remington: The Science and Practice of Pharmacy.* 20th edition, ISBN: 0683306472.
[28] *Vaccine Design* . . . (1995) eds. Powell & Newman. ISBN: 030644867X. Plenum.
[29] Loza et al. (2010) *Int. J. STD AIDS* 21:460-465
[30] *Methods In Enzymology* (S. Colowick and N. Kaplan, eds., Academic Press, Inc.)
[31] *Handbook of Experimental Immunology*, Vols. I-IV (D. M. Weir and C. C. Blackwell, eds, 1986, Blackwell Scientific Publications)
[32] Sambrook et al. (2001) *Molecular Cloning: A Laboratory Manual,* 3rd edition (Cold Spring Harbor Laboratory Press).
[33] *Handbook of Surface and Colloidal Chemistry* (Birdi, K. S. ed., CRC Press, 1997)
[34] Ausubel et al. (eds) (2002) *Short protocols in molecular biology,* 5th edition (Current Protocols).
[35] *Molecular Biology Techniques: An Intensive Laboratory Course*, (Ream et al., eds., 1998, Academic Press)
[36] PCR (*Introduction to Biotechniques Series*), 2nd ed. (Newton & Graham eds., 1997, Springer Verlag)
[37] Geysen et al. (1984) *PNAS USA* 81:3998-4002.
[38] Carter (1994) *Methods Mol Biol* 36:207-23.
[39] Jameson, B A et al. 1988, *CABIOS* 4(1):181-186.
[40] Raddrizzani & Hammer (2000) *Brief Bioinform* 1(2):179-89.
[41] Bublil et al. (2007) *Proteins* 68(1):294-304.
[42] De Lalla et al. (1999) *J. Immunol.* 163:1725-29.
[43] Kwok et al. (2001) *Trends Immunol* 22:583-88.
[44] Brusic et al. (1998) *Bioinformatics* 14(2):121-30
[45] Meister et al. (1995) *Vaccine* 13(6):581-91.
[46] Roberts et al. (1996) *AIDS Res Hum Retroviruses* 12(7):593-610.
[47] Maksyutov & Zagrebelnaya (1993) *Comput Appl Biosci* 9(3):291-7.
[48] Feller & de la Cruz (1991) *Nature* 349(6311):720-1.
[49] Hopp (1993) *Peptide Research* 6:183-190.
[50] Welling et al. (1985) *FEBS Lett.* 188:215-218.
[51] Davenport et al. (1995) *Immunogenetics* 42:392-297.
[52] Tsurui & Takahashi (2007) *J Pharmacol Sci.* 105(4):299-316.
[53] Tong et al. (2007) *Brief Bioinform.* 8(2):96-108.
[54] Schirle et al. (2001) *J Immunol Methods.* 257(1-2):1-16.
[55] Chen et al. (2007) *Amino Acids* 33(3):423-8.
[56] *Current Protocols in Molecular Biology* (F. M. Ausubel et al., eds., 1987) Supplement 30
[57] Smith & Waterman (1981) *Adv. Appl. Math.* 2: 482-489.
[58] STI Surveillance Team. Sexually transmitted infections in New Zealand: Annual Surveillance Report 2008. Porirua, New Zealand: Institute of Environmental Science and Research Limited; 2009.
[59] The Institute of Environmental Science and Research Ltd. Sexually transmitted infections in New Zealand. Annual Surveillance Report 2013. Porirua, New Zealand: The Institute of Environmental Science and Research Ltd; 2014.
[60] Jackson et al. (2011) *Arch. Dis. Child.* 96:744-751.
[61] Creighton et al. (2003) *International journal of STD & AIDS* 14:109-113.
[62] Bromhead et al. (2013) *J. Clin. Microbiol.* 51:1505-1509.
[63] Vonck et al. (2011) *Infection and Immunity* 79:1566-1577.
[64] Hedges et al. (1998) *J. Infect. Dis.* 178:742-51.
[65] Manhart et al. (2004) *Am. J. Epidemiol.* 160:393-402.

The invention claimed is:

1. A method for immunizing a subject against *Neisseria gonorrhoeae* by administering to the subject an immunogenic composition according to a multiple dose schedule, the method comprising:

administering to the subject the immunogenic composition, wherein the immunogenic composition comprises meningococcal outer membrane vesicles (OMVs) from *Neisseria meningitidis* serogroup B strain NZ98/254; and administering the immunogenic composition to the subject to induce a cross-reactive immune response against *Neisseria gonorrhoeae*, wherein the subject is 12 to 18 or 18 years or older and is at increased risk of infection with *Neisseria gonorrhoeae* relative to the average risk in the general population, and wherein the subject has been previously immunized against *N. meningitidis*, and wherein the immunogenic composition is used to treat *Neisseria gonorrhoeae* in the subject.

2. The method of claim 1, wherein the composition includes an adjuvant.

3. The method of claim 1, wherein the composition includes an aluminium salt adjuvant.

4. The method of claim 1, wherein the composition is free of thiomersal.

5. The method of claim 1, wherein the composition is administered to the subject by intramuscular injection.

6. The method of claim 1, wherein the subject has previously been fully immunized against *N. meningitidis* and the immunogenic composition is administered as a booster to protect against *N. gonorrhoeae*.

7. The method of claim 1, wherein the subject is co-immunized against human papillomavirus (HPV).

8. The method of claim 1, wherein the subject is seropositive for *N. gonorrhoeae*.

9. The method of claim 1, wherein the cross-reactive immune response comprises a CD4+T cell response against *Neisseria gonorrhoeae*.

10. The method of claim 9, wherein administration of the immunogenic composition increases the level of Interferon-gamma (IFN-γ) as compared to administration of a control without the OMVs.

11. The method of claim 9, wherein administration of the immunogenic composition increases the level of Interleukin-17 (IL-17) as compared to administration of a control without the OMVs.

12. The method of claim 1, wherein the cross-reactive immune response comprises inducing bactericidal antibodies against *Neisseria gonorrhoeae*.

13. The method of claim 1, wherein the subject is not co-infected with *Chlamydia*.

14. The method of claim 1, wherein a booster dose of the immunogenic composition is administered to the subject to treat *Neisseria gonorrhoeae* in the subject.

15. The method of claim 1, wherein the subject was previously immunized in childhood.

16. The method of claim 1, wherein the subject receives a booster dose of the immunogenic composition to treat *Neisseria gonorrhoeae*.

* * * * *